United States Patent
Thomas et al.

(12)

(10) Patent No.: US 6,342,344 B1
(45) Date of Patent: Jan. 29, 2002

(54) ANTIBODY COMPOSITION FOR ISOLATING HUMAN CELLS FROM HUMAN-MURINE CHIMERIC HEMATOPOIETIC CELL SUSPENSIONS

(75) Inventors: Terry E. Thomas; Connie J. Eaves, both of Vancouver (CA)

(73) Assignee: StemCell Technologies Inc., Vancouver (CA)

( * ) Notice: Subject to any disclaimer, the term of this patent is extended or adjusted under 35 U.S.C. 154(b) by 0 days.

(21) Appl. No.: 09/363,677

(22) Filed: Jul. 30, 1999

Related U.S. Application Data (60) Provisional application No. 60/094,844, filed on Jul. 31, 1998.

(51) Int. Cl.[7] .......................... A01N 1/02; G01N 33/567; C12N 5/08
(52) U.S. Cl. ................... 435/2; 435/7.21; 435/354; 435/355; 435/366; 435/372; 435/373
(58) Field of Search ................ 435/2, 7.21, 354, 435/355, 366, 372, 373

(56) References Cited

PUBLICATIONS

Cashman, J., et al., Br. J. Haematol. (1997) 97:1026–1036. Sustained proliferation, multi–lineage differentiation and maintenance of primitive human hematopoietic cells in NOD/SCID mice transplanted with human cord blood.

Cashman, J.D., et al., Blood (1997) 89:4307–4316. Kinetic evidence for regeneration of multi–lineage hematopoiesis from primitive cells in normal human bone marrow transplanted into immunodeficient mice.

*Primary Examiner*—David Saunders
*Assistant Examiner*—Mary Beth Tung
(74) *Attorney, Agent, or Firm*—Micheline Gravelle Bereskin & Parr (57) ABSTRACT

The present invention relates to an antibody composition which contains antibodies directed to murine leukocyte and murine erythroid cells. This composition is used in a novel negative selection process to enrich for human hematopoietic cells from a sample from human-murine chimeric mice. The invention also relates to kits for carrying out this process.

9 Claims, 5 Drawing Sheets

ANTIBODY COMPOSITION FOR ISOLATING HUMAN CELLS FROM HUMAN-MURINE CHIMERIC HEMATOPOIETIC CELL SUSPENSIONS

This application claims benefit from U.S. provisional application Ser. No. 60/094,844 filed on Jul. 31, 1998 which is incorporated herein by reference in its entirety.

FIELD OF THE INVENTION

The present invention provides novel antibody compositions and negative selection processes for enriching human cells from murine/human chimeric haematopoietic cell suspension.

BACKGROUND OF THE INVENTION

Human cells are often transplanted into mice in order to study various diseases as the study of human cells in such diseases cannot always be adequately modelled in vitro.

Human/Murine transplant chimeras have been used to study human autoimmune diseases, such as Graves disease (Yoshikawa, N. et al., 1997; Weetman, A. P., 1996). Chimeric mice have also been used to evaluate the efficacy of anti-viral agents in the treatment of human immunodeficiency virus (HIV) and Epstein Barr Virus (EBV) (Jenkins M. et al., 1998; Fuzzati-Armentero, M. T., 1998). However, in such models it has been difficult to efficiently retrieve human cells from the chimeric mice to enable further assays.

Human/Murine chimeric mice are also used to study hematopoietic stem cells. The hematopoietic stem cell is identified by its distinct functional capabilities, including self-renewal and long-term repopulation of all hematopoietic lineages. In vitro assays, such as long-term culture-initiating cells (LTC-IC) (Sutherland, H. J., et al., 1989) are not entirely predictive of repopulating and homing potential in vivo and therefore, several groups have transplanted human hematopoietic stem cells into RAG–/– (Koyanagi, Y. et al., 1997) or severe combined immune deficiency (SCID) mice (McCune, J. M. et al., 1988; Kamel-Reid S. and Dick J. E., 1988; Kyoizumi S. et al., 1992; Larochelle, A., et al., 1996); or non obese diabetic SCID (NOD.SCID) (Cashman, J. D., et al. 1997). The surviving transplanted human cells and their progeny may be very rare in bone marrow and blood. This creates difficulties in determining the success of engraftment and makes further functional assay of the surviving engrafted human cells not feasible. Therefore, there is a need to develop a method to enrich for human cells allowing the detection and isolation of these low frequency human cells in chimeric SCID/Hu, NOD.SCID/Hu or RAG–/–/Hu mice.

SUMMARY OF THE INVENTION

The present inventors have developed an antibody composition for use in enriching human cells from human-murine chimeric hematopoietic cell suspensions. The antibodies in the antibody composition are specific for selective markers associated with murine cells.

In particular, the present inventors have found that a negative selection technique using an antibody composition containing an antibody specific for murine leukocytes (such as anti-CD45 and/or anti major histocompatibility complex class I (MHC-I)) alone or in combination with an antibody capable of binding to murine erythroid cells gives a cell preparation highly enriched for human cells. Accordingly, the present invention provides an antibody composition comprising an antibody specific for murine leukocytes and an antibody specific for murine erythroid cells.

Preferably, the present invention provides an antibody composition comprising an antibody specific for murine CD45 and an antibody capable of binding to a murine erythroid cells. CD45 is a pan-leukocyte maker expressed on all hematopoietic cells with the exception of erythroid cells (Ledabetter, J.A and Herzenburg, L.A., Immunol. Rev. 47:63 (1979); Thomas, M. L. Ann. Rev. Immunol. 7:339–369 (1989); Van Ewijk, W. et al., J. Immnumol. 127:2594 (1981)). Human cells will be enriched from human-murine chimeric hematopoietic cell suspension by depleting only $CD45^+$ murine cells although the presence of murine erythroid cells will limit the degree of enrichment. Combining an antibody which recognizes murine erythroid cells with an anti-murine CD45 antibody will deplete all murine hematopoietic cells and thereby achieve extensive enrichment of human cells thus enabling detection and further study.

The enrichment and recovery of human cells using the antibody composition of the invention in a negative selection technique has many advantages over conventional positive selection techniques. Most importantly, the recovered human cells are not labelled or coated with antibodies thereby making them highly suitable for further study.

The present invention includes a negative selection process for enriching and recovering human cells in a sample containing human cells and murine cells comprising:
 (a) reacting the sample with an antibody composition containing antibodies capable of binding to murine leukocytes under conditions such that conjugates are formed between the antibodies and murine leukocytes;
 (b) removing the conjugates; and
 (c) recovering a cell population which is enriched in human cells and depleted of murine leukocytes.

In a preferred embodiment, the present invention provides
 (a) reacting the sample with an antibody composition containing antibodies capable of binding to murine leukocytes and antibodies capable of binding to murine erythroid cells under conditions such that conjugates are formed between the antibodies and the murine leukocytes and murine erythroid cells;
 (b) removing the conjugates; and
 (c) recovering a cell population which is enriched in human cells and depleted of murine leukocytes and murine erythroid cells.

The present invention also includes a kit useful in performing the process of the invention comprising antibodies specific for murine leukocytes and murine erythroid cells and instructions for performing the process of the invention.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

I. Antibody Composition

As hereinbefore mentioned, the present invention relates to an antibody composition comprising an antibody specific for murine leukocytes in combination with an antibody specific for murine erythroid cells. Preferably, the antibody specific for murine leukocytes is anti-CD45 or anti-MHC-I and the antibody specific for murine erythroid cells is TER119.

Within the context of the present invention, antibodies are understood to include monoclonal antibodies and polyclonal antibodies, antibody fragments (e.g., Fab, and F(ab')$_2$) and recombinantly produced binding partners.

Polyclonal antibodies against selected antigens on the surface of murine cells may be readily generated by one of ordinary skill in the art from a variety of warm-blooded animals such as horses, cows, various fowl, rabbits or rats.

Preferably, monoclonal antibodies are used in the antibody compositions of the invention. Monoclonal antibodies specific for selected antigens on the surface of murine cells may be readily generated using conventional techniques (see U.S. Pat. No. RE 32,011, U.S. Pat. Nos. 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are incorporated herein by reference).

Other techniques may also be utilized to construct monoclonal antibodies (see William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," Proc Natl. Acad. Sci USA 86:5728–5732, August 1989; see also Michelle Alting-Mees et al., "Monoclonal Antibody Expression Libraries: A Rapid Alternative to Hybridomas," Strategies in Molecular Biology 3:1–9, January 1990; these references describe a commercial system available from Stratacyte, La Jolla, Calif., which enables the production of antibodies through recombinant techniques).

Similarly, binding partners may be constructed utilizing recombinant DNA techniques. Within one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources. The primers may be utilized to amplify heavy or light chain variable regions, which may then be inserted into vectors such as ImmunoZAP™ H or ImmunoZAP™ L (Stratacyte), respectively. These vectors may then be introduced into *E. coli* for expression. Utilizing these techniques, large amounts of a single-chain protein containing a fusion of the VH and VL domains may be produced (See Bird et al., Science 242:423–426, 1988). In addition, such techniques may be utilized to change a "murine" antibody to a "human" antibody, without altering the binding specificity of the antibody.

Antibodies against selected antigens on the surface of murine cells may also be obtained from commercial sources. In this regard, antibodies against murine CD45 include Pharmingen clone 30-F11, Caltag clone YW62.3, Serotec clone YW62-3 and Sigma clone 13-2. Antibodies to murine MHC-I include Deveron clone KDH3, UMRD Inc. clone H58A, Bachem Bioscience clones ERHR52 and ERMPH2. Antibodies against murine erythroid cells include Pharmingen clone TER119 (Ikuta, K. et al., Cell 62:863–874; Ogawa, M. et al. J. Exp. Med. 174:63–71). The anti-murine CD45 antibody depletes CD45 positive murine cells. Tests have shown that the above clones 30-F11 and TER119 do not bind human cells. The TER119 antibody recognizes murine erythroid cells.

II. Method of the Invention

The present invention includes a negative selection process for enriching and recovering human cells in a sample containing human cells and murine cells comprising:

(a) reacting the sample with an antibody composition containing antibodies capable of binding to murine leukocytes under conditions such that conjugates are formed between the antibodies and murine leukocytes;

(b) removing the conjugates; and (c) recovering a cell population which is enriched in human cells and depleted of murine leukocytes.

In a preferred embodiment, the present invention provides (a) reacting the sample with an antibody composition containing antibodies capable of binding to murine leukocytes and antibodies capable of binding to murine erythroid cells under conditions such that conjugates are formed between the antibodies and the murine leukocytes and murine erythroid cells;

(b) removing the conjugates; and (c) recovering a cell population which is enriched in human cells and depleted of murine leukocytes and murine erythroid cells.

The sample can be any sample from a human/murine chimeric mouse including, but not limited to, blood, bone marrow, spleen, thymus, liver and lymph node samples.

Conditions which permit the formation of cell conjugates may be selected having regard to factors such as the nature and amounts of the antibodies in the antibody composition, and the estimated concentration of targeted murine cells in the sample.

The antibodies in the antibody composition may be labelled with a marker or they may be conjugated to a matrix. Examples of markers are biotin, which can be removed by avidin or anti-biotin antibody bound to a support, and fluorochromes, e.g. fluorescein, which provide for separation using fluorescence activated sorters. Examples of matrices are magnetic beads, which allow for direct magnetic separation (Kemshead 1992), panning surfaces, e.g., plates, (Lebkowski, J. S, et al., (1994), J. of Cellular Biochemistry supple. 18b:58), dense particles for density centrifugation (Van Vlasselaer, P., Density Adjusted Cell Sorting (DACS), A Novel Method to Remove Tumor Cells From Peripheral Blood and Bone Marrow StemCell Transplants. (1995) 3rd International Symposium on Recent Advances in Hematopoietic Stem Cell Transplantation-Clinical Progress, New Technologies and Gene Therapy, San Diego, Calif.), adsorption columns (Berenson et al. 1986, Journal of Immunological Methods 91:11–19.), and adsorption membranes (Nordon et al. 1994). The antibodies may also be joined to a cytotoxic agent such as complement or a cytotoxin, to lyse or kill the targeted murine cells.

The antibodies in the antibody composition may be directly or indirectly coupled to a matrix. For example, the antibodies in the composition of the invention may be chemically bound to the surface of magnetic particles using, for example cyanogen bromide. When the magnetic particles are reacted with a sample conjugates will form between the magnetic particles with bound antibodies specific for antigens on the surfaces of the murine cells, and the murine cells having the antigens on their surfaces.

Alternatively, the antibodies may be indirectly conjugated to a matrix using antibodies. For example, a matrix may be coated with a second antibody having specificity for the antibodies in the antibody composition. By way of example, if the antibodies in the antibody composition are mouse IgG antibodies, the second antibody may be rabbit anti-mouse IgG.

The antibodies in the antibody composition may also be incorporated in antibody reagents which indirectly conjugate to a matrix. Examples of antibody reagents are bispecific antibodies, tetrameric antibody complexes, and biotinylated antibodies.

Bispecific antibodies contain a variable region of an antibody in the antibody composition of the invention, and a variable region specific for at least one antigen on the surface of a matrix. The bispecific antibodies may be prepared by forming hybrid hybridomas. The hybrid hybridomas may be prepared using the procedures known in the art such as those disclosed in Staerz & Bevan, (1986, PNAS (USA) 83: 1453) and Staerz & Bevan, (1986, Immunology Today, 7:241). Bispecific antibodies may also be constructed by chemical means using procedures such as those described by Staerz et al., (1985, Nature, 314:628) and Perez et al., (1985 Nature 316:354), or by expression of recombinant immunoglobulin gene constructs.

A tetrameric immunological complex may be prepared by mixing a first monoclonal antibody which is capable of binding to at least one antigen on the surface of a matrix, and a second monoclonal antibody from the antibody composition of the invention. The first and second monoclonal antibodies are from a first animal species. The first and second antibodies are reacted with an about equimolar amount of monoclonal antibodies of a second animal species which are directed against the Fc-fragments of the antibodies of the first animal species. The first and second antibodies may also be reacted with an about equimolar amount of the F(ab')$_2$ fragments of monoclonal antibodies of a second animal species which are directed against the Fc-fragments of the antibodies of the first animal species. (See U.S. Pat. No. 4,868,109 to Lansdorp, which is incorporated herein by reference for a description of tetrameric antibody complexes and methods for preparing same).

The antibodies of the invention may be biotinylated and indirectly conjugated to a matrix which is labelled with (strept) avidin. For example, biotinylated antibodies contained in the antibody composition of the invention may be used in combination with magnetic iron-dextran particles that are covalently labelled with (strept) avidin (Miltenyi, S. et al., Cytometry 11:231, 1990). Many alternative indirect ways to specifically cross-link the antibodies in the antibody composition and matrices would also be apparent to those skilled in the art.

In an embodiment of the invention, the cell conjugates are removed by magnetic separation using magnetic particles. Suitable magnetic particles include particles in ferrofluids and other colloidal magnetic solutions. "Ferrofluid" refers to a colloidal solution containing particles consisting of a magnetic core, such as magnetite ($Fe_3O_4$) coated or embedded in material that prevents the crystals from interacting. Examples of such materials include proteins, such as ferritin, polysaccharides, such as dextrans, or synthetic polymers such as sulfonated polystyrene cross-linked with divinylbenzene. The core portion is generally too small to hold a permanent magnetic field. The ferrofluids become magnetized when placed in a magnetic field. Examples of ferrofluids and methods for preparing them are described by Kemshead J. T. (1992) in J. Hematotherapy, 1:35–44, at pages 36 to 39, and Ziolo et al. Science (1994) 257:219 which are incorporated herein by reference. Colloidal particles of dextran-iron complex are preferably used in the process of the invention. (See Molday, R. S. and McKenzie, L. L. FEBS Lett. 170:232, 1984; Miltenyi et al., Cytometry 11:231, 1990; and Molday, R. S. and MacKenzie, D., J. Immunol. Methods 52:353, 1982; Thomas et al., J. Hematother. 2:297 (1993); and U.S. Pat. No. 4,452,733, which are each incorporated herein by reference).

Figure 1:
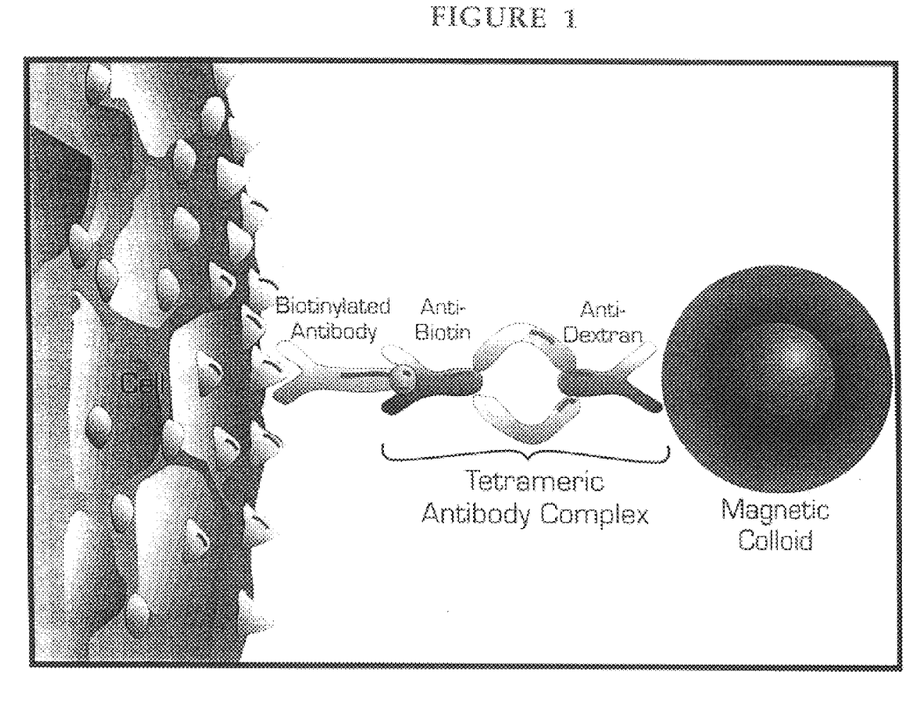
FIG. 1 is a schematic drawing of magnetic labelling of murine cells.
Figure 2:
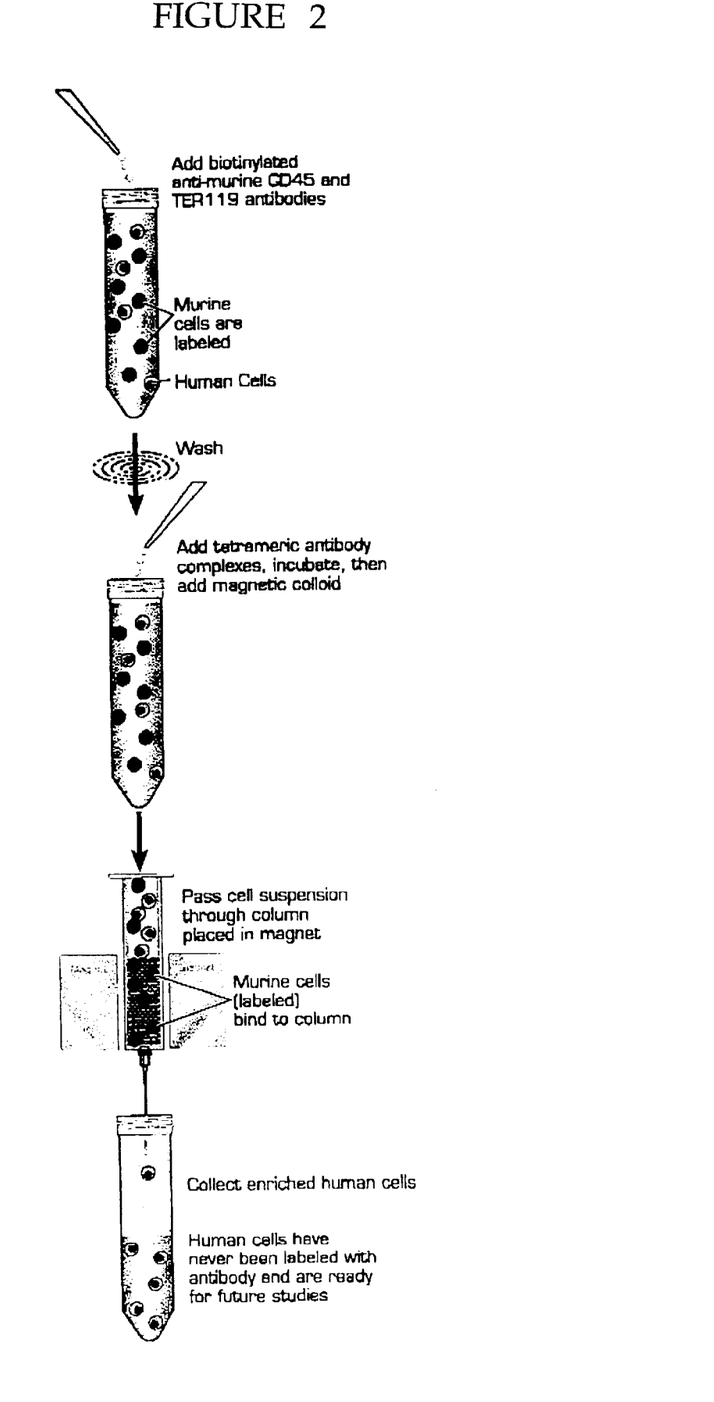
FIG. 2 is a schematic drawing illustrating the enrichment method the invention.

FIG. 1 is a schematic representation of magnetic cell labelling using biotinylated antibodies, tetrameric antibody complexes and colloidal dextran iron.

In accordance with the magnetic separation method, the sample containing the human cells to be recovered, is reacted with the above described antibody reagents, preferably tetrameric antibody complexes and biotinylated anti-mouse antibodies, so that the antibody reagents bind to the targeted murine cells present in the sample to form cell conjugates of the targeted murine cells and the antibody reagents.

Cells are first labelled with biotinylated anti-CD45 and TER119, washed and then incubated with tetrameric antibody complexes followed by magnetic colloid. The reaction conditions are selected to provide the desired level of binding of the targeted murine cells and the antibody reagents. Preferably the sample is incubated with the antibody reagents for a period of 5 to 60 minutes at either 4–8° C. or ambient room temperature. The concentration of the antibody reagents are selected to optimize cell labelling in a sample of $2-8\times10^7$ in nucleated cells per ml. Generally, the concentration is between about 0.1 to 50 µg/ml of sample. The magnetic particles are then added and the mixture is incubated for a period of about 5 minutes to 30 minutes at the selected temperature although the time may be longer or shorter depending upon condition chosen. The sample is then ready to be separated over a magnetic filter device. Preferably, the magnetic separation procedure is carried out using the magnetic filter and methods described in U.S. Pat. No. 5,514,340 to Lansdorp and Thomas which is incorporated in its entirety herein by reference.

The sample containing the magnetically labelled cell conjugates is passed through the magnetic filter in the presence of a magnetic field. In a preferred embodiment of the invention, the magnet is a permanent gap magnet with a 0.5–2.0 inch gap and having a magnetic field of 0.5–2 Tesla. The magnetically labelled cell conjugates are retained in the high gradient magnetic column and the materials which are not magnetically labelled flow through the column after washing with a buffer.

The preparation containing non-magnetically labelled cells may be analyzed using procedures such as flow cytometry. The ability of the cells in the preparation to produce colony-forming cells or LTC-IC in culture may also be assessed. The efficiency of the separation procedure may also be determined by monitoring the recovery of human CD45+ cells.

III. Uses of the Composition and Processes of the Invention

The composition and processes of the invention may be used in the processing of samples including marrow and spleen from human/murine chimeric mice. Using the processes of the invention it is possible to recover a highly purified preparation of human cells from the human/murine chimeric mice for the purpose of studying, human stem cells; human hematopoietic disease; human immune function, development and pathophysiology; human responses to infection; and transplantation biology.

The present invention also includes a kit useful in performing the process of the invention comprising antibodies specific for murine leukocytes and murine erythroid cells and instructions for performing the process of the invention.

The following non-limiting examples are provided for illustration of the present invention.

EXAMPLES

Example 1

Methodology

Human cells may be recovered from chimeric mouse marrow or spleen using the antibody composition of the invention containing biotinylated antibodies (anti-CD45 and TER119) directed against all murine hematopoietic cells. The labelled cells are linked to magnetic dextran-iron particles via bispecific anti-biotin anti-dextran tetrameric antibody complexes. FIG. 1 illustrates the indirect magnetic labelling of murine cells. Cells are first labelled with a cocktail of biotinylated antibodies directed against murine cell surface markers. Murine cells are then cross-linked to magnetic dextran iron particles using tetrameric antibody complexes comprised of two murine $IgG_1$ monoclonal antibodies held in tetrameric array by two rat anti-mouse $IgG_1$ monoclonal antibody molecules. One murine antibody molecule recognizes biotin and the other recognizes dextran on the magnetic particle. The immunomagnetically labelled murine cells are then removed from the cell suspension in a magnetic column leaving a cell suspension enriched for unlabelled human hematopoietic cells. The magnetically labelled murine cells bind to the column.

Flow Cytometry

Human cells were detected by FACS analysis following staining with a combination of FITC labelled anti-human CD45 (leukocytes) antibody and PE labelled anti-human CD71 (erythrocytes) antibody. Murine cells were detected with a combination of anti-murine CD45 antibody and TER119 antibody. Human subsets were detected by double staining with the appropriate FITC labelled anti-human antibodies (anti CD3 and anti CD34).

Chimeric Mice

The SCID mutation or RAG knockout results in failure of the VDJ joining mechanism during rearrangement of antigen receptor genes. Consequently, RAG knockout and CB-17 mice homozygous for the SCID mutation lack functional B and T cells (Bosma, G. C., Nature, 301:527, 1983; Bosma, M. J. and Carroll, A. M., Ann. Rev. Immunol., 9:323, 1991; Koyanagi, Y. et al., Leukemia, 11:109–112, 1997). SCID and RAG-/- mice do, however, possess normal NK and myeloid function which can limit the survival of cells transplanted into these mice (Mosier, D. E. et al., Nature, 335:256, 1988; McCune, J. M., et al., Science, 241:1632, 1988). The SCID mutation was therefore back-crossed onto the NOD/Lt mouse, which is defective in innate immune function. The resultant NOD/SCID mouse is defective in both lymphoid and myeloid function and will readily accept the long-term survival of human hematopoietic cells (Shultz, L. D. et al., J. Immunol., 154:180, 1995).

Results

Verification of Specificity

Figure 3:
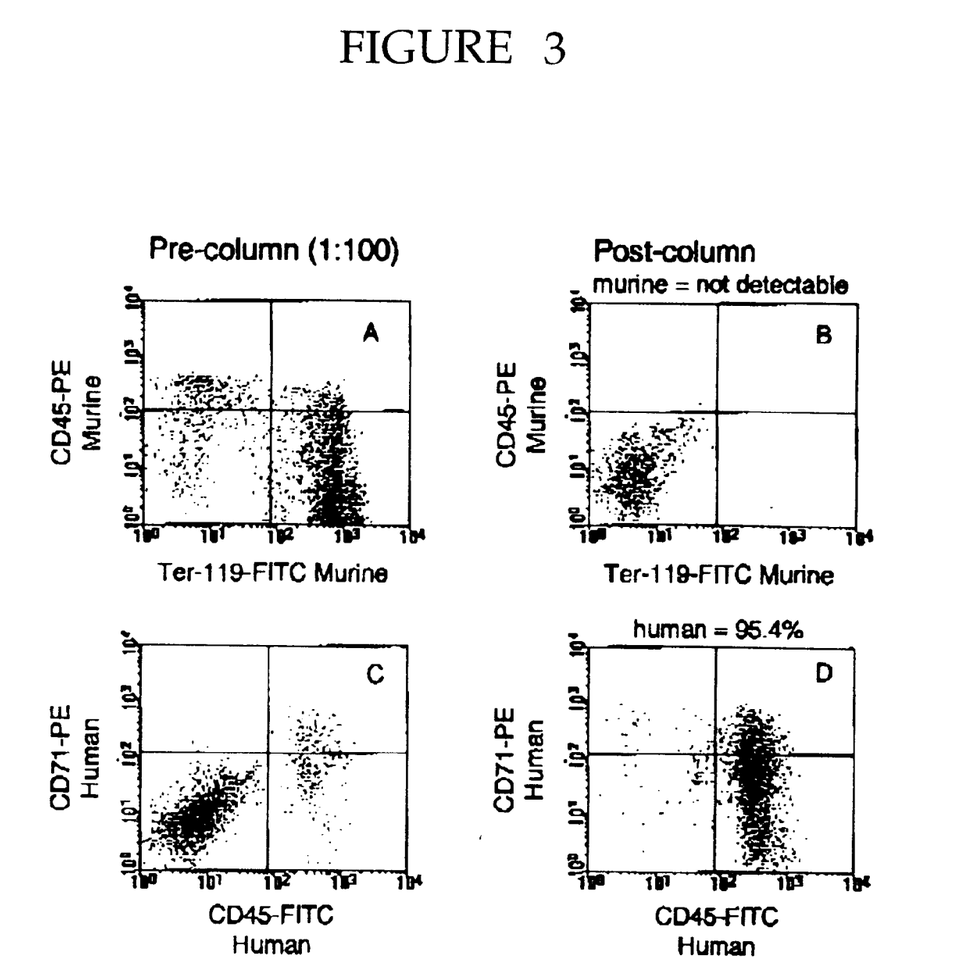
FIG. 3 is a FACS profile showing murine marrow cells seeded with human cord blood cells (1:100) before (A and C) and after (B and D) processing using the method of the invention.

Normal human cord blood mononuclear cells (HCMC) were seeded into NOD/SCID bone marrow suspensions at human:murine cell ratios of 1:1, 1:10 or 1:100. Human cells were then recovered from the mixture using the method of the invention and detected by FACS as shown in FIG. 3. FACS plots show staining of 1:100 mixtures of human cells and mouse marrow before (A and C) and following (B and D) enrichment of human cells. Cells were stained with anti-murine CD45 and TER119 (A and B) or with anti-human CD45 and CD71 (C and D). The recovery of various types of human and murine cells is given in Table 1.

Isolation of Human Cells from Transplanted Mice

NOD/SCID mice were irradiated with a sub-lethal dose of radiation prior to intravenous injection of $2 \times 10^7$ to $2 \times 10^8$ HCMC (equivalent to 0.7 to $3 \times 10^6$ CD34+ cells). Six weeks later NOD/SCID bone marrow was harvested and human cells were detected by FACS. Without enrichment of human cells, mice transplanted with higher doses ($3 \times 10^6$) of CD34+ cells were found to be successfully engrafted with human cells. In contrast, mice transplanted with lower doses ($0.7 \times 10^6$) of CD34+ cells were minimally positive or negative for human cells. Following depletion of murine cells using the method of the invention, human cells were clearly detected by FACS in the marrow of these low dose CD34 mice.

Figure 4:
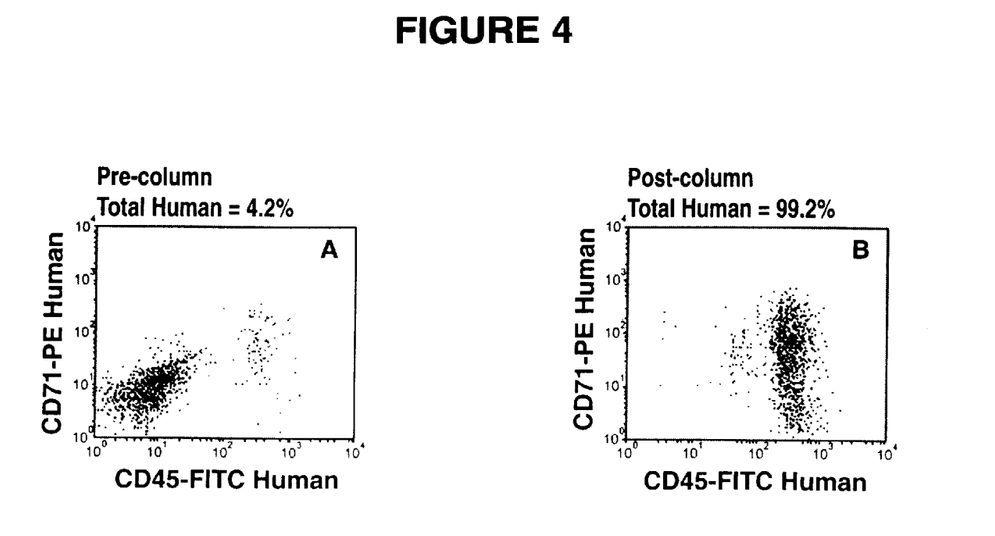
FIG. 4 is a FACS profile showing cells from chimeric murine bone marrow before (A) and after (B) depletion of murine cells using the method of the invention.

FIG. 4 and Table 2 show the enrichment and recovery of CD45+ human cells from chimeric mouse bone marrow using the method of the invention. FIG. 4 illustrates the low level of engraftment of human cells in these chimeric mice which was barely detectable prior to enrichment (A) was the vast majority of events following enrichment of human cells using the method of the invention (B). Cells were stained with anti-human CD45 and anti-CD71. Table 3 shows the percent recovery of various populations of human and murine cells using the method of the invention to enrich for human cells.

Detection and Isolation of Rare Human Hematopoietic Cell Subsets

Figure 5:
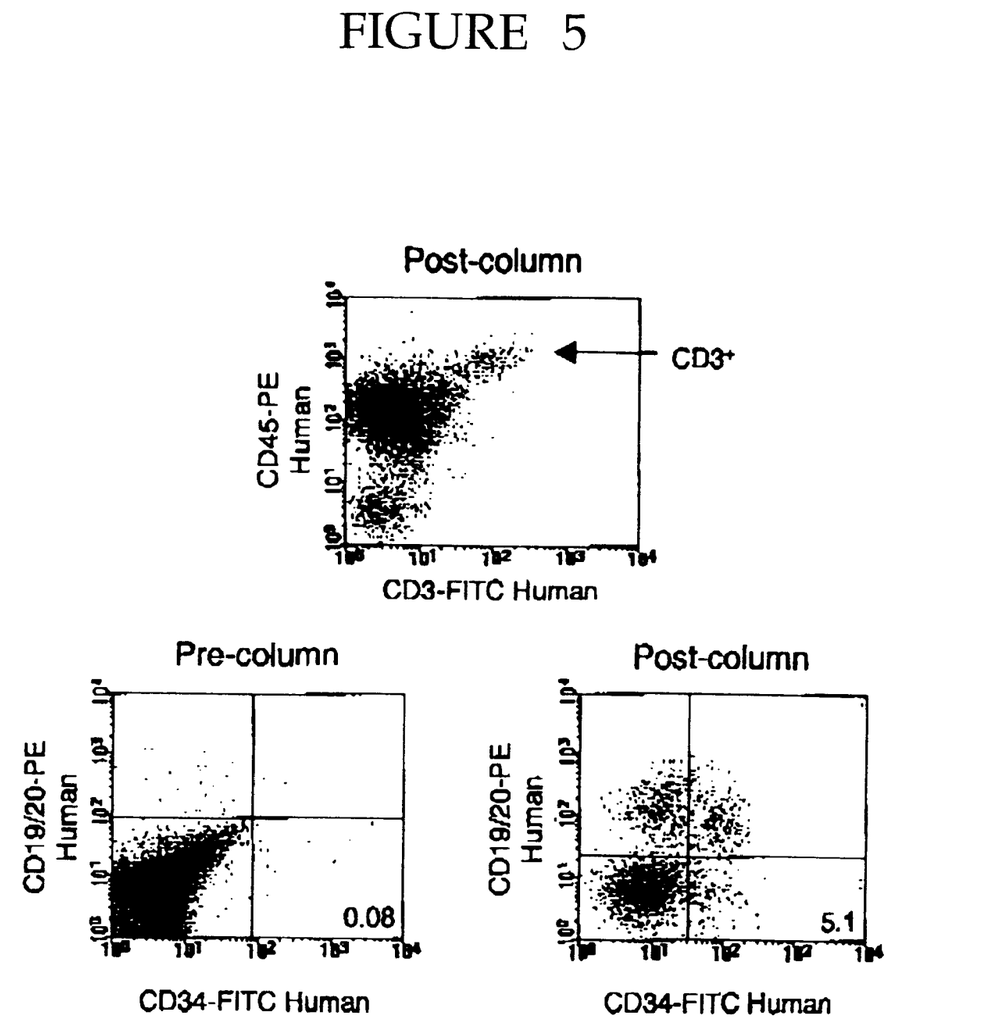
FIG. 5 is a FACS profile of marrow cells from human/murine (NOD/SCID) chimeric bone marrow before (pre-column) and, after (post-column) depletion of murine cells using the method of the invention. Human CD3$^+$ and human CD34$^+$ cells are detected.

The enrichment of subpopulates of human cells in SCID/Hu bone marrow is often too low to detect or sort using FACS. Following enrichment using the method of the invention, minor populations of human cells were detected by FACS. The inventors demonstrated the presence of CD3+ and CD34+ human cells in the marrow of engrafted mice. These populations were not detectable by FACS prior to enrichment (FIG. 5).

Enrichment of Human Cells for Functional Studies

Typically $10^9$ SCID/Hu bone marrow cells are required to produce the minimal number of human cells needed in functional assays. This is beyond the capacity of most FAC sorters but can be easily accommodated with the method of the invention. The marrows from several SCID/Hu mice are pooled and using the method of the invention, sufficient unlabelled human cells were obtained to perform colony assays in methylcellulose. The resultant colonies were found to be exclusively human using standard cytogenetic techniques. Table 4 shows the human colony forming cell (CFC) assay results for the bone marrow of four individual chimeric mice. Prior to processing none of the bone marrow suspensions had sufficient human cells to plate in the CFC assay. Following enrichment of human cells with the method of the invention human colonies were detected in all four samples.

Conclusions

The antibody composition of the invention was able to specifically deplete murine cells providing a suspension of viable human cells in sufficient numbers to perform functional and phenotypic analyses. This facilitated detection of human cells in mice and hence assessment of engraftment. Enrichment of human cells also allowed the detection and isolation of rare subsets of human cells.

All publications, patents and patent applications are herein incorporated by reference in their entirety to the same extent as if each individual publication, patent or patent application was specifically and individually indicated to be incorporated by reference in its entirety.

While what is shown and described herein constitutes various preferred embodiments of the subject invention, it will be understood that various changes can be made to such embodiments without departing from the subject invention, the scope of which is defined in the appended claims.

DETAILED REFERENCES

Bosma G C: A severe combined immunodeficiency mutation in the mouse. Nature 301:527, 1983.

Bosma M J, Carroll A M: The SCID mouse mutant: Definition, characterization and potential uses. Ann. Rev. Immunol. 9:323, 1991.

Cashman J D, Bockhold K, Hogge D E, Eaves A C, Eaves C J: Sustained proliferation, multi-lineage differentiation and maintenance of primitive human haemopoietic cells in NOD/SCID mice transplanted with human cord blood. Br. J. Haematol. 97:1026, 1997.

Fuzzati-Armentero M T, Duchosal M A: hu-PBL-SCID mice: An in vivo model of Epstein-Barr virus-dependent lymphoproliferative disease. Histol Histopathol, 13:155, 1998.

Ikuta K et al. (1990). Cell 62:863–874. A developmental shift in thymic lymphocyte maturation potential occurs at the level of hematopoietic stem cells.

Jenkins M, Hanley M B, Moreno M B, Wieder E, McCune J M: Human immunodeficiency virus-1 infection interrupts thymopoiesis and multilineage hematopoiesis in vivo. Blood 91:2672, 1998.

Kamel-Reid S, Dick J E: Engraftment of immune-deficient mice with human hematopoietic stem cells. Science 242:1706, 1988.

Koyanagi Y, Tanaka Y, Tanaka R, Misawas N, Kawano Y, Tanaka T, Miyaskaa M, Ito M, Veyama Y, Yamamoto N. Leukemia High levels of viremia in chimeric mice with HIV-1 infection, 11:109–112, 1997.

Kyoizumi S, Baum C M, Kaneshima H, McCune J M, Yee E J, Namikawa R: Implantation and maintenance of functional human bone marrow in SCID-hu mice. Blood 79:1704, 1992.

Larochelle A, Vormoor J, Hanenberg H, Wang J C Y, Bhatia M, Lapidot T, Moritz T, Murdoch B, Xiao X L, Kato I, Williams D A, Dick J E: Identification of primitive human hematopoietic cells capable of repopulating NOD/SCID mouse bone marrow: Implications for gene therapy. Nature Medicine 2:1329, 1996.

Ledbetter J A and Herzenburg L A, Xenogenic monoclonal antibodies to mouse lymphoid differentiation antigen, Immunol Rev 47:63, 1979.

Kemshead, J of Hematotherapy, Vol. 1:35–44, 1992.

McCune J M, Namikawa R, Kaneshima H, Shultz L D, Lieberman M, Weissman I L: The SCID-Hu mouse: Murine model for the analysis of human hematolymphoid differentiation and function. Science 241:1632, 1988.

Mosier D E, Gulizia R J, Baird S M, Wilson D B: Transfer of a functional human immune system to mice with severe combined immunodeficiency. Nature 335:256, 1988.

Nordon R E, Milthorpe B K, Schindhelm K, and Slowiaczek P R: An Experimental Model of Affinity Cell Separation. Cytometry 16:25–33, 1994.

Ogawa M et al. (1991). J. Exp. Med. 174:63–71. Expression and function of c-kit in hemopoietic progenitor cells.

Shultz L D, Schweitzer P A, Christianson S W, Gott B, Schweitzer I B, Greiner D L, Leiter E H: Multiple defects in innate and adaptive immunologic function in NOD/LtSz-scid Mice. J. Immunol. 154:180, 1995.

Sutherland H J, Eaves C J, Eaves A C, Dragowska W, Lansdorp P M: Characterization and partial purification of human marrow cells capable of initiating long-term hematopoiesis in vitro. Blood 74:1563, 1989.

Thomas M L, Ann Rev Immunol, 7:339–369, 1989.

Van Ewijk W et al., Fluorescence analysis and anatomical distribution of mouse T lymphocyte subsets defines by MAb to the antigens Thy-1, Lyt-2 and T-200, J. Immunol, 127:2594, 1981.

Weetman A P: The SCID mouse model: a discussion. Exp Clin Endocrinol Diabetes, 104:40, 1996.

Yoshikawa N, Nishikawa M, Mori S, Toroko T. Yamamoto Y, Ikehara S, Kumazawa H, Yamashita T, Inada M: Simultaneous xenotransplantation of human Graves thyroid tissue and autologous bone marrow cells in severe combined immunodeficient mice: Successful reconstitution of human Graves hyperthyroidism. Eur J. Endocrinol 136:213, 1997.

TABLE 1

Recovery of Various Types of Murine and Human Cells after Immunomagnetic Depletion of the Murine Cells from Artificial Mixtures of Human Cord Blood and Murine Marrow Cells

| | | Percent Recovery | | |
|---|---|---|---|---|
| Populations Analyzed | | Mixtures with 50% | Mixtures with 10% | Mixtures with 1% |
| Genotype | Phenotype | Human Cells | Human Cells | Human Cells |
| Human | $CD45/71^+$ | 84 ± 14 | 61 ± 13 | 58 ± 5 |
| | $CD34^-CD19/20^+$ | 67 ± 0 | 48 ± 3 | 75 ± 16 |
| | $CD45/71^+/CD15^+$ | 99 | 50 ± 11 | 56 ± 7 |
| | $CD34^+$ | 74 ± 6 | 90 ± 19 | 140 ± 40 |
| Mouse | $CD45^+$ | <0.2 | <0.05 | <0.03 |
| | $Ter-119^+$ | 0.04 | <0.06 | <0.03 |

Values shown are the mean±SEM of values from 4 experiments in 2 of which a 50% mixture was not included. Where no errors are shown, only a single measurement was made. In many of the experiments, murine $CD45^+$ or $Ter-119^+$ cells, if present, were below the threshold set for this assay (<5/5000 positive events over background). In these instances, a number equivalent to the threshold value was used to calculate upper limits (designated as < values).

TABLE 2

The recovery of human $CD45^+$ cells from chimeric mouse marrow following enrichment of human cells using the method of the invention.

| | % Human $CD45^+$ Cells | | % Recovery |
|---|---|---|---|
| | Pre-Column | Post-Column | Human $CD45^+$ Cells |
| Mouse 1 | 4.2 | 98.0 | 58 |
| Mouse 2 | 64.9 | 98.0 | 61 |
| Mouse 3 | 3.6 | 99.5 | 86 |
| Mouse 4 | 8.8 | 98.5 | 94 |
| Mouse 5 | 20.6 | 98.9 | 43 |
| Mouse 6 | 48.0 | 99.4 | 85 |

TABLE 3

Percent Recovery of Various Populations of Human and Mouse Cells During Depletion of Mouse Cells from Marrow Cells Harvested from NOD/SCID Mice Engrafted with Human Cells.

| Populations Analyzed | | Percent Recovery | |
|---|---|---|---|
| Geonotype | Phenotype | Experiment 1 | Experiment 2 |
| Human | $CD45^+/71^+$ | 59 ± 6 | 94 ± 14 |
| | $CD34^-CD19^+/20^+$ | 68 ± 9 | 100 ± 10 |
| | $CD45^+/71^+CD15^+$ | 29 ± 5 | 57 ± 18 |
| | $CD34^+$ | 45 ± 5 | 97 ± 19 |
| | CFC | 47 ± 15 | ND |
| Mouse | $CD45^+$ | <0.08 | <0.1 |
| | $Ter-119^+$ | <0.2 | <0.1 |

Values shown are the mean±SEM of values for marrows harvested and processed individually from 4 and 6 mice per experiment (no. 1 and 2, respectively). Zero values (from mouse cell analyses) were treated as described in the footnote to Table 1. ND=Note done.

TABLE 4

The detection of human colony forming cells (CFC) in the marrow of chimeric mice following enrichment of human cells (post-column) using the method of the invention.

| | Total Colonies Counted | | | |
|---|---|---|---|---|
| | Pre-Column | Post-Column | Cells Plated | Cytogenics |
| Mouse 1 | ND | 13 | $5 \times 10^4$ | Hu |
| Mouse 2 | ND | 32 | $10^4$ | Hu |
| Mouse 3 | ND | 113 | $10^4$ | Hu |
| Mouse 4 | ND | 149 | $10^4$ | Hu |

ND: Insufficient human cells are present in the pre-column samples to allow plating in CFC assays

We claim:

1. A negative selection process for enriching and recovering human cells in a sample containing human cells and murine cells comprising:
    (a) reacting the sample with an antibody composition containing antibodies capable of binding to murine leukocytes under conditions such that conjugates are formed between the antibodies and murine leukocytes wherein the antibodies capable of binding to murine leukocytes are selected from anti-CD45 and anti-MHC-I;
    (b) removing the conjugates; and
    (c) recovering a cell population which is enriched in human cells and depleted of murine leukocytes.

2. A process according to claim 1 further comprising adding TER119 antibodies capable of binding to murine erythroid cells in step (a) and recovering a cell population which is enriched in human cells and depleted of murine hematopoietic cells in step (c).

3. A process according to claim 1 wherein the antibody capable of binding to murine leukocytes is a murine anti-CD45 antibody.

4. A process according to claim 2 wherein the antibodies are monoclonal antibodies.

5. A process as claimed in claim 4 wherein the antibodies are labelled with a marker or they are conjugated to a matrix.

6. A process as claimed in claim 4 wherein the antibodies are labelled with biotin or fluorochrome.

7. A process as claimed in claim 5 wherein the matrix is magnetic beads, a panning surface, dense particles for density centrifugation, an adsorption column, or an adsorption membrane.

8. A process as claimed in claim 7, wherein each of the monoclonal antibodies to the murine leukocytes and murine erythroid cells is incorporated in a tetrameric antibody complex wherein each tetrameric antibody complex comprises a first monoclonal antibody of a first animal species can bind either leukocytes or erythroid cells, and a second monoclonal antibody of the first animal species which is capable of binding to at least one antigen on the surface of a matrix, which have been conjugated to form a cyclic tetramer with two monoclonal antibodies of a second animal species directed against the Fc-fragments of the antibodies of the first animal species.

9. A process as claimed in claim 8 wherein each of the monoclonal antibodies is biotinylated and coupled to a separation matrix via a tetrameric antibody complex which recognises biotin and the matrix.

* * * * *